United States Patent [19]

Choi et al.

[11] Patent Number: 5,492,829
[45] Date of Patent: Feb. 20, 1996

[54] KLEBSIELLA OXYTOCA NO. 19-1 CAPABLE OF PRODUCING α-CYCLODEXTRIN

[75] Inventors: Jang Youn Choi, Bucheon; Jae Ho Lee, Seoul; Kee Hyuh Choi, Seoul; Ik Boo Kwon, Seoul, all of Rep. of Korea

[73] Assignee: Lotte Confectionery Co., Ltd., Seoul, Rep. of Korea

[21] Appl. No.: 36,212

[22] Filed: Mar. 23, 1993

Related U.S. Application Data

[63] Continuation-in-part of Ser. No. 811,112, Dec. 20, 1991, abandoned.

[30] Foreign Application Priority Data

Dec. 20, 1990 [KR] Rep. of Korea ............... 90-21177

[51] Int. Cl.$^6$ .................. C12N 1/20; C12P 19/18
[52] U.S. Cl. .................. 435/252.1; 435/97; 435/822
[58] Field of Search .................. 435/252.1, 97, 435/822

[56] References Cited

U.S. PATENT DOCUMENTS

| | | | |
|---|---|---|---|
| 3,425,910 | 2/1969 | Armbruser et al. | 435/97 |
| 3,640,847 | 2/1972 | Armbruster et al. | 435/97 |
| 3,652,398 | 3/1972 | Armbruster et al. | 435/97 |
| 3,934,598 | 12/1975 | Horikoshi et al. | 195/31 R |
| 4,317,881 | 4/1982 | Yagi et al. | 435/97 |
| 4,835,105 | 5/1989 | Seres et al. | 435/97 |
| 4,921,796 | 5/1990 | Ruzzell | 436/97 |
| 5,178,863 | 1/1993 | Toyoda et al. | 435/252.1 |

FOREIGN PATENT DOCUMENTS

| | | | |
|---|---|---|---|
| 0017242 | 4/1980 | European Pat. Off. | C12P 19/18 |
| 0045464 | 7/1981 | European Pat. Off. | C08B 37/16 |
| 3330571 | 4/1984 | Germany | C12N 9/24 |
| 8901043 | 2/1989 | WIPO | 435/97 |

OTHER PUBLICATIONS

Analytical Viochemistry 181, 6–1 (1989).
Bergey's Manual of Systematic Bacteriology, (1984) vol. 1, pp. 461–465.
Bergey's Manual of Determinative Bacteriology, 9th ed., (1994), pp. 181, 210, 211, 226, 227 and 235.

*Primary Examiner*—Herbert J. Lilling
*Attorney, Agent, or Firm*—Cushman Darby & Cushman

[57] ABSTRACT

The particular strain of *Klebsiella oxytoca* No. 19-1 has been isolated from soil which produces a cyclomaltoglucanotransferase enzyme capable of converting starch to α-cyclodextrin in very high proportion, nearly close to 100 percent, rather than another types of cyclodextrins.

6 Claims, 6 Drawing Sheets

KLEBSIELLA OXYTOCA NO. 19-1 CAPABLE OF PRODUCING α-CYCLODEXTRIN

REFERENCE TO RELATED APPLICATION

This is a continuation-in-part of application No. 07/811,112, filed Dec. 20, 1991, which was abandoned in favor hereof.

BACKGROUND OF THE INVENTION

The present invention relates to a newly isolated strain of *Klebsiella oxytoca* No. 19-1 which is capable of producing α-cyclodextrin in high proportion, nearly close to 100 percent, from starch.

Cyclodextrins (cycloamyloses, cyclomaltaoses, Schardinger dextrins, CDs) are cyclic, nonreducing oligossccharides composed of glucose units linked by α-1,4 glycosidic bonds. They are called α-, β-, or γ- cyclodextrin depending on the number of glucose units: 6, 7 or 8, respectively.

Cyclodextrins have been shown to act as host molecules, having a torus in the molecule capable of forming inclusion complexes with various kinds of organic compounds. This specific ability has been widely used in the field of food, pharmaceuticals, agricultural chemistry, cosmetics, and perfumes.

Cyclodextrins are produced from starch and related compounds by cyclomaltodextrin glucanotransferase (E.C.2.4.1.19: CGTase). Some microorganisms, such as *Bacillus marcerans, Bacillus megaterium, Bacillus stearothermophilus, Bacillus circulans, Bacillus spp., Klebsiella pneumoniae* M5a1, *Micrococcus sp.*, and *Thermoanaerobacter sp.*, are also known to produce CGTase.

Although all CGTase produced by these microorganisms can convert starch to cyclodextrins, their characteristics is different from each other. Accordingly, even if a bacterium is known for a typical strain which is producing α-cyclodextrin, it does not produce α-cyclodextrin only, but produces another types of cyclodextrins at the same time. It is, therefore, still required to complicated purification process in preparation of each cyclodextrin in high degree of purity.

In the conventional process, raw starch is usually liquefied by heating in the presence or absence of starch—hydrolyzing enzyme, and CGTase is added to liquefied starch for the synthesis of cyclodextrins. Since the distribution of produced cyclodextrins can be controlled by reaction or process conditions, there have been trials to increase the yield of a special cyclodextrin. For example, in the formation of cyclodextrin from starch by CGTase, the addition of organic compounds such as n-decanol is known to lead to an increase in α-cyclodextrin yield. But in this case, the effect of n-decanol on α-cyclodextrin yield is not significant to all kinds of CGTase: the use of n-decanol seems not to be favorable when one attempts to produce α-cyclodextrin with *B. macerans* CGTase (Starch/Starke, 41,417–420, 1989). In addition to, it was reported that organic solvents such as toluene, ethanol, n-butanol, and propanol increased the production yield of cyclodextrins in the conventional process. However, the use of toxic solvents like toluene and decanol seems to be undesirable since cyclodextrins produced in the presence of these solvents are prohibited in food, cosmetics, and pharmaceuticals.

Since β-cyclodextrin is readily separated from the reaction mixture without any treatment with organic solvents and its inclusion complexes can be easily prepared owing to its low solubility in water, β-cyclodextrin among the three common types of cyclodextrins, is more widely used and developed for applications. For practical use, however, cyclodextrins should be available at a reasonable price, much effort has been focused on finding a suitable CGTase for the efficient production of β-cyclodextrin through screening of microorganisms.

As a consequence, the price of β-cyclodextrin dropped drastically during the last decade. But cyclodextrins can not be used interchangably because of their different property, and α- as well as γ-cyclodextrin is still relatively expensive material for applications in industry, since the purification of α- and γ-cyclodextrin is more complicated than that of β-cyclodextrin (for example, gel filtration processes) and often accomplished by precipitation with organic solvent.

α-Cyclodextrin may be classified as dietary fiber and is effective as a calorie substitute for weight control. Therefore, its extensive application is expected in the food and pharmaceutical industries. It is desirable to develop a novel CGTase that produces α-cyclodextrin in high proportion, nearly close to 100 percent from starch, so that the price of α-cyclodextrin can be more suitable for applications by simplifying the manufacturing processes of α-cyclodextrin without an additional gel filtration process or treatment with harmful organic solvent.

Accordingly, it is an object of the present invention to provide an enzyme which converts starch to α-cyclodextrin in very high proportion, nearly close to 100 percent, rather than another types of cyclodextrins.

It is another object of the present invention to provide a microorganism which is able to produce an enzyme capable of converting starch to α-cyclodextrin in high proportion, nearly close to 100 percent, rather than another types of cyclodextrins.

SUMMARY OF THE INVENTION

The present invention aims to provide an enzyme which is capable of converting starch to a mixture of cyclodextrins, the proportion of α-cyclodextrin of which occupies at least 95% of the total weight of the cyclodextrin mixture.

The present inventors have succeeded in identifying an enzyme which converts starch to α-cyclodextrin in very high proportion, nearly close to 100 percent, rather than another types of cyclodextrins.

The enzyme of the present invention is produced by a bacterium which has been isolated from soil by the present inventors. It has been discovered that a newly isolated bacterium belongs to the genus Klebsiella. The particular Klebsiella strain preferred as enzyme source is further identified as *Klebsiella oxytoca,* named herein *Klebsiella oxytoca* No. 19-1, and have been deposited with the Korean Cultured Center and Microorganism (KCCM) on Nov. 23, 1990 as deposit number of KCCM 10002.

Another object of the present invention is to provide a microorganism which is able to produce an enzyme, termed CGTase, capable of converting starch to a mixture of cyclodextrins, the proportion of α-cyclodextrin of which occupies at least 95% of the total weight of the cyclodextrin mixture.

The microorganism capable of producing the enzyme has the taxonomical characteristics of *Klebsiella oxytoca* according to a preferred embodiment of the invention.

When the CGTase produced by *Klebsiella oxytoca* No. 19-1 was used according to reaction conditions in the formation of α-cyclodextrin from starch, exemplified in the present invention, it is possible to obtain high purity of α-cyclodextrin, at least 95% of the total weight of the cyclodextrins mixture, and to eliminate complicated processes, such as gel filtration and solvent precipitation, currently used in manufacturing α-cyclodextrin.

Accordingly, the CGTase provided in the present invention is greatly useful in the formation of α-cyclodextrin and conventional process may be used without limit.

DESCRIPTION OF THE PREFERRED EMBODIMENT

Figure 1:
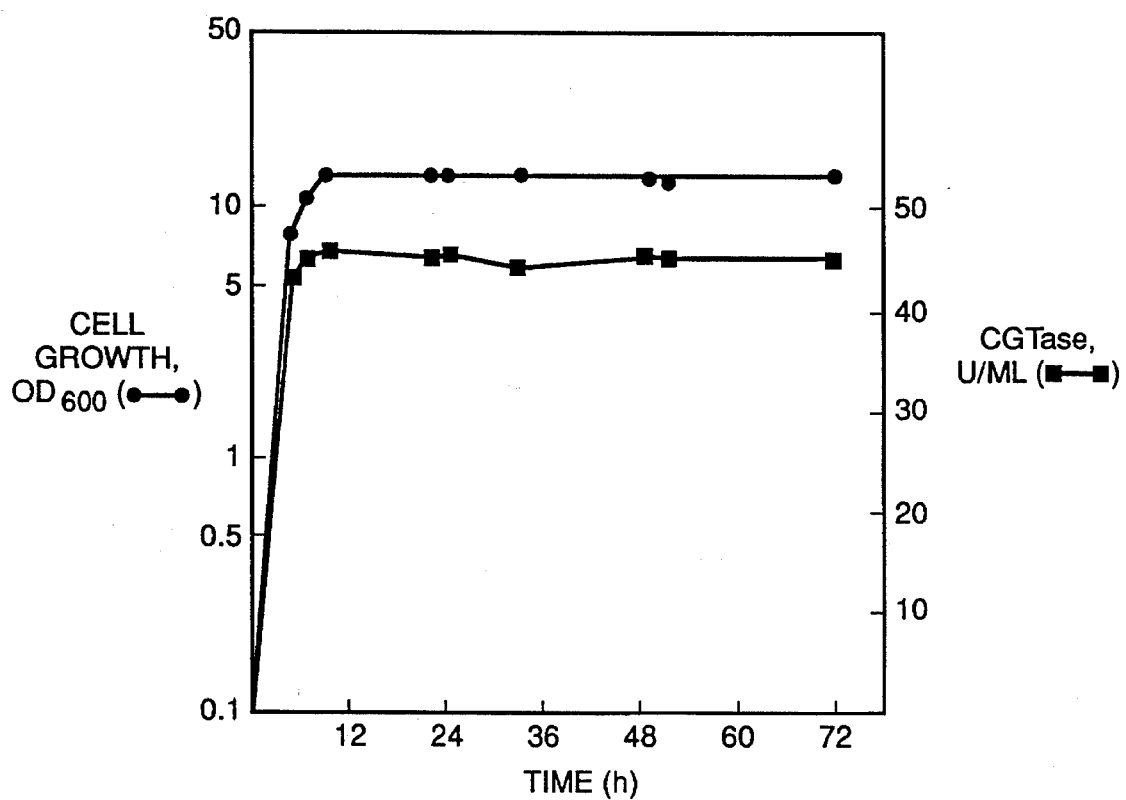
FIG. 1, the CGTase reaches its maximum activity after 9 hr cultivation and further increase of activity was not observed after that time.

The particular strain of *Klebsiella oxytoca* No. 19-1 was isolated from soil which was collected from Kosung County, Kyungsangnam Province, Korea by the present inventors in 1990.

Taxonomical study of the strain was performed according to Bergey's Manual of Systematic Bacteriology and API 20E Kit(France).

Taxonomical characteristics of *Klebsiella oxytoca* No. 19-1 is as follows:

1. Morphological characteristics
    Vegetable cell: short-rod, 0.3~0.1 μm×0.6~3 μm
    Motility: non-motile
    Spore: not formed
    Gram staining: negative
2. Cultural characteristics
    Nutrient agar plate: good growth, some protuberance and smoothness, dampness, having colony of lemon yellow.
    Nutrient agar slant: good growth, growing on the whole of slant.
    MacConkey agar plate: good growth, having colony of red pink color.
3. Physiological characteristics
    pH for growth: 4~9
    Temperature for growth: 10°~35° C.
    Behavior to oxygen: facultative anaerobic
    Hydrolysis of starch: positive
    Hydrolysis of casein: negative
    Hydrolysis of carboxy methyl cellulose: negative
    Hydrolysis of pullulan: positive
    Hydrolysis of pectate (Star medium): positive
    Liquefaction of gelatin: negative
    Citrates utilization: positive
    V.P. test: positive
    Indole production: positive
    $H_2S$ production: positive
    M.R. test: negative
    Catalase: positive
    Oxidase: negative
    Urease: positive
    α-Galactosidase: positive
    Reduction of nitrate: positive
    Production of pigments: negative
    Tryptophane desaminase: negative
    Lysine decarboxylase: positive
    Ornithine decarboxylase: negative
    Arginine dihydrolase: negative
    Fecal coliform test: negative
    [Acid production from various sugars]
    Glucose: positive
    Mannitol: positive
    Inositol: positive
    Sorbitol: positive
    Rhamnose: positive
    Sucorse: positive
    Melibiose: positive
    Amygdalin: positive
    Arabinose: positive It is clear that it belongs to Klebsiella genus and most closely resembles the species of *Klebsiella oxytoca* on the basis of the above data. This particular strain of *Klebsiella oxytoca* No. 19-1 is considered to be different from other known CGTase-producing species of Klebsiella, because of its pectate degradation ability, growth at 10° C., and result of fecal coliform test.

By standard culture methods of microorganisms, the enzyme of the present invention can be produced by the strain. The new strain is inoculated in a composited or natural medium, and cultivated with shaking.

The medium should consist of starch or amylopectin as a carbon source, and in addition to that, a nitrogen source and inorganic salts may be used without limit. The strain is cultivated at the temperature range of 30° to 40° C. under the aerobic condition after the medium of pH is adjusted to about 7.

The enzyme should be prepared in suitable forms to be useful in the formation of cyclodextrins from starch. Extracellular medium where cells excreting the enzyme have been removed by general methods, filtration or centrifugation, can be used. Another form to be useful is concentrated or fractionated form. It can be made by ultrafiltration, precipitation with appropriate solvents or chemicals, chromatographic separation, or a combination thereof in order to provide the increased enzyme concentration. The other form is the lyophilized which is made by reconstitution of raw or concentrated extracellular medium with appropriate buffer after lyophilization.

Reaction conditions in the formation of cyclodextrins from starch by CGTase are similar to known processes. The starch used in practicing the present invention may be derived from any vegetable source, for example, corn, wheat, potato, tapioca, and rice. Waxy starch, modified starch, dextrins, soluble or pregelatinized starch are also suitable in the formation of cyclodextrins by CGTase.

Following are the examples to illustrate the present invention in further detail but not to limit the scope of the invention.

EXAMPLE 1

This example illustrates isolation of the particular strain of *Klebsiella oxytoca* No. 19-1. Soil samples collected from various locations around Kosung County were used. One drop of soil suspension was spreaded on a minimal agar plate (1.5% agar, 1% soluble starch, 0.2% $(NH_4)_2SO_4$, 0.02% $MgSO_4 \cdot 7H_2O$ in 50 mM phosphate buffer (pH 8.0)) and incubated at 37° C. for 48 hr. After starch-hydrolyzing colonies were selected by treatment of iodine vapor, they were transferred to LS broth (L-broth plus 1% soluble starch) and cultivated for 48 hr at 37° C. One milliliter of supernatant from each cultured broth was mixed with a half milliliter of 3% soluble starch solution and incubated for 10 hr at 37° C. The presence of α-cyclodextrin in the reaction mixture was then determined by thin-layer chromatography described in example 2, and further analyzed by the methyl orange method and HPLC described in example 3.

EXAMPLE 2

This example illustrates conditions of thin-layer chromatography. Five microliter of each reaction mixture was spotted onto DC-Plstikfolien Kiegelgel$_{60}$F$_{254}$ (Merck, Germany) with standard cyclodextrins. n-butanol/ethanol/water (4/3/3 parts in volume) was used as a developing solvent. The plate was stained with 1% methanolic iodine, and both Rf value and color characteristics of stained spots were compared with those of standard cyclodextrins. Thus, reaction mixture of which spot revealed yellow color and Rf value was very similar to that of standard α-cyclodextrin, was selected and further analyzed according to the methods described in example 3.

EXAMPLE 3

This example illustrates the process of assay of CGTase and determination of α-cyclodextrin. The activity of CGTase was measured according to the method of Lejeune, A. et al. (Analytical Biochemistry, 181, p. 6–11, 1989). One milliliter of approximately diluted enzyme was incubated with 0.6 ml of 5% (w/v) soluble starch, 0.105 ml of 1 mM methyl orange and 1.295 ml of 50 mM phosphate buffer (pH 6) at 37° C. for 10 min.

The reaction was ceased by addition of 0.150 ml of 6N HCl and maintained at 15° C. on a water bath for 30 min. By determination of optical density at 507 nm, the activity of the enzyme could be calculated with the prepared standard curve.

One unit of the enzyme activity was defined as the amount of enzyme which produces 1 μmole of α-cyclodextrin per minute under the given conditions.

The profile and content of cyclodextrins were determined by HPLC under following conditions: carbohydrate analysis column (Waters Assoc., USA), acetonitrile/water (65/35), flow rate 2.0 ml/min, and RI detector. Samples to be analyzed the amount of produced α-cyclodextrin were taken and boiled for 10 min to inactivate the enzyme. Samples were also treated with acetonitrile to make final concentration to 65%, same to eluent, and filtered through a membrane (0.45 μm, Millipore, USA) to remove remaining substrate, starch.

EXAMPLE 4

This example illustrates production and purification of the enzyme, CGTase. *Klebsiella oxytoca* No. 19-1 was cultivated aerobically in 1 L of the medium containing 1% starch, 1% polypeptone, 0.1% $K_2HPO_4$, 0.02% $MgSO_4$; 37° C., pH 7, 0.5 vvm, 400 rpm, 9 hr.

As shown in FIG. 1, the CGTase reaches its maximum activity after 9 hr cultivation and further increase of activity was not observed after that time.

After the removal of cells by centrifugation (6000×g, 5 min) supernatant was treated with three volumes of ethanol and maintained at 4° C. for overnight.

The formed precipitate was collected by centrifugation (6000 g, 10 min, 4° C.), suspended in 50 mM phosphate buffer (pH 6.0), and dialyzed against same buffer for overnight. This dialyzed enzyme solution was applied to a column of DEAE—Sepharose CL—6B equilibrated with 50 mM acetate buffer (pH 5.5). After washing the column with the same buffer, elution was carried out with 200 mM NaCl. CGTase active fractions were then mixed and the activity of enzyme was tested.

TABLE 1

| step | Volumn(ml) | Total activity (Units × $10^3$) | Specific activity (Units/mg) | Yield (%) | Fold |
| --- | --- | --- | --- | --- | --- |
| Culture broth | 1,000 | 50.2 | 29.4 | 100 | 1 |
| Ethanol precipitation | 100 | 38.5 | 220.4 | 77 | 7.5 |
| DEAE-Sepharose | 20 | 27.6 | 1380.2 | 55 | 46.9 |

Purification of the CGTase from *Klebsiella oxytoca* No. 19-1.

EXAMPLE 5

This example illustrates properties of purified CGTase. Purified CGTase was assayed for its activity of α-cyclodextrin formation from starch in various pH and temperature range (pH 4–6, 50 mM acetate buffer; pH 6–8, 50 mM phosphate buffer; pH 8–10, 50 mM glycine-NaOH buffer).

Figure 2A:
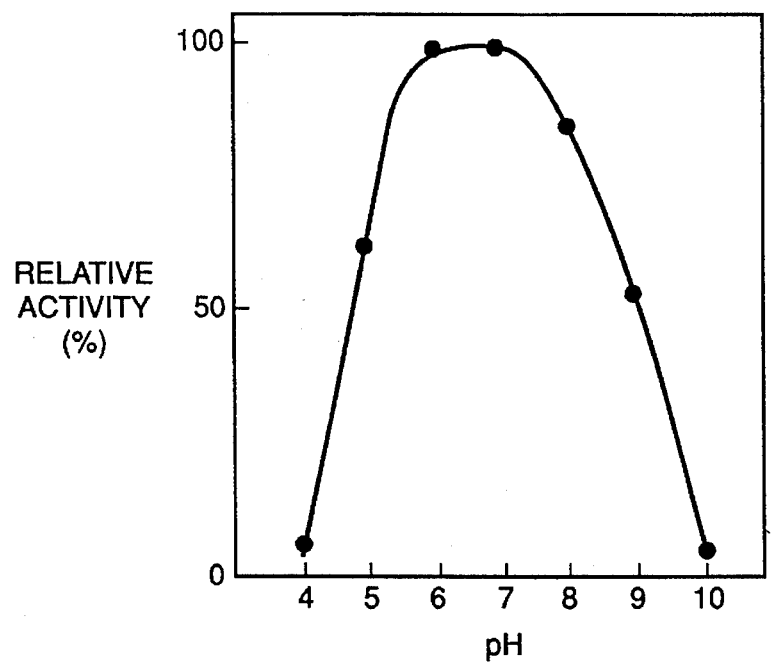
FIG. 2A, the CGTase reveals that its optimum pH range is 5.5–7.5 and its maximum activity shows at around pH 6.0, and that no activity is found below pH 4.0 or above 10.0.

As shown in FIG. 2A, the CGTase reveals that its optimum pH range is 5.5–7.5 and its maximum activity shows at around pH 6.0, and that no activity is found below 4.0 or above 10.0.

Figure 2B:
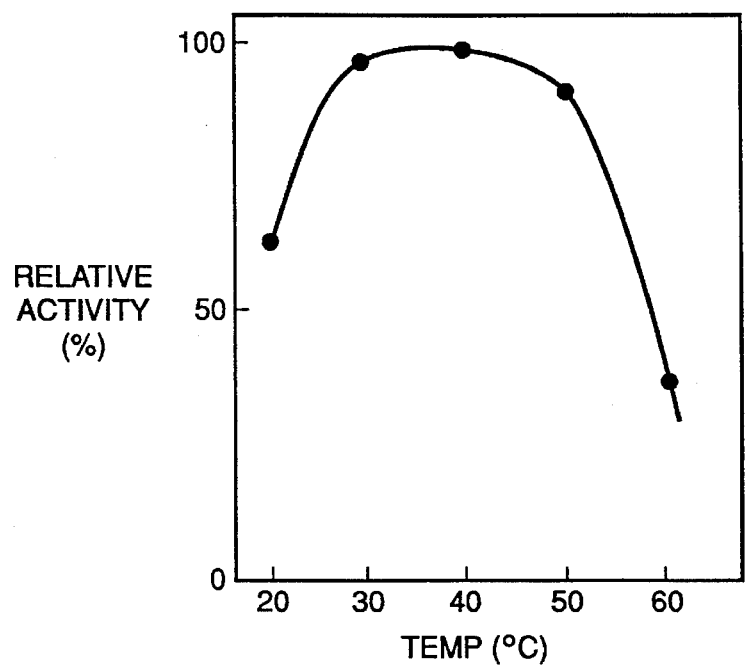
FIG. 2B shows the results of activity according to various temperature at pH 6.0. The CGTase is most active in the broad range of 30°–50° C., and the maximum activity of the CGTase was observed around 45°–50° C.

FIG. 2B shows the results of activity according to various temperature at pH 6.0. The CGTase is most active in the broad range of 30°–50° C., and the maximum activity of the CGTase was observed around 45°–50° C.

Figure 3A:
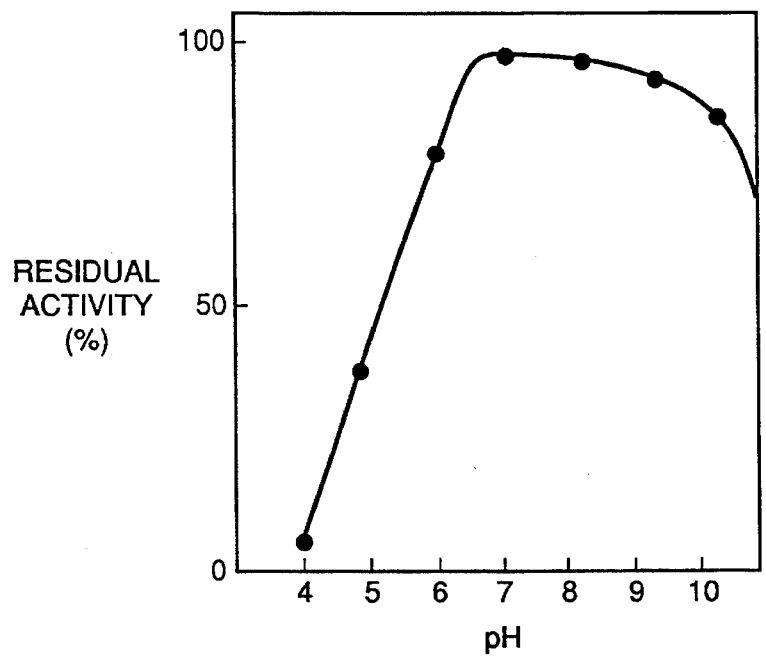
FIG. 3A shows the results of pH stability performed on above described buffer solution at 37° C. for 1 hr.

FIG. 3A shows the results of pH stability performed on above described buffer solution at 37° C. for 1 hr. The CGTase reveals stability around pH range of 6.0 to 10.0.

Figure 3B:
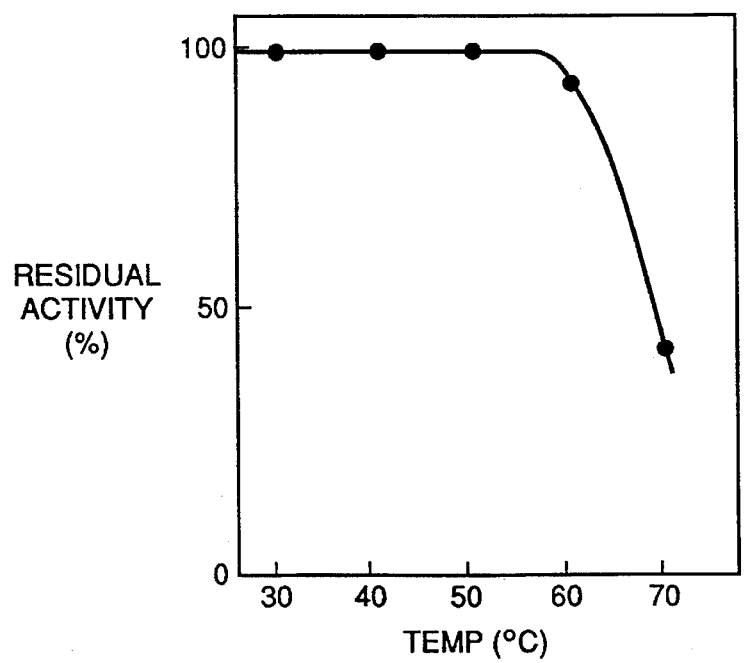
FIG. 3B shows the results of heat stability when the purified CGTase was held at various temperature for 20 min in 50 mM phosphate buffer (pH 6.0).

FIG. 3B shows the results of heat stability when the purified CGTase was held at various temperature for 20 min in 50 mM phosphate buffer (6.0). The CGTase reveals its heat stability up to 60° C.

Figure 4:
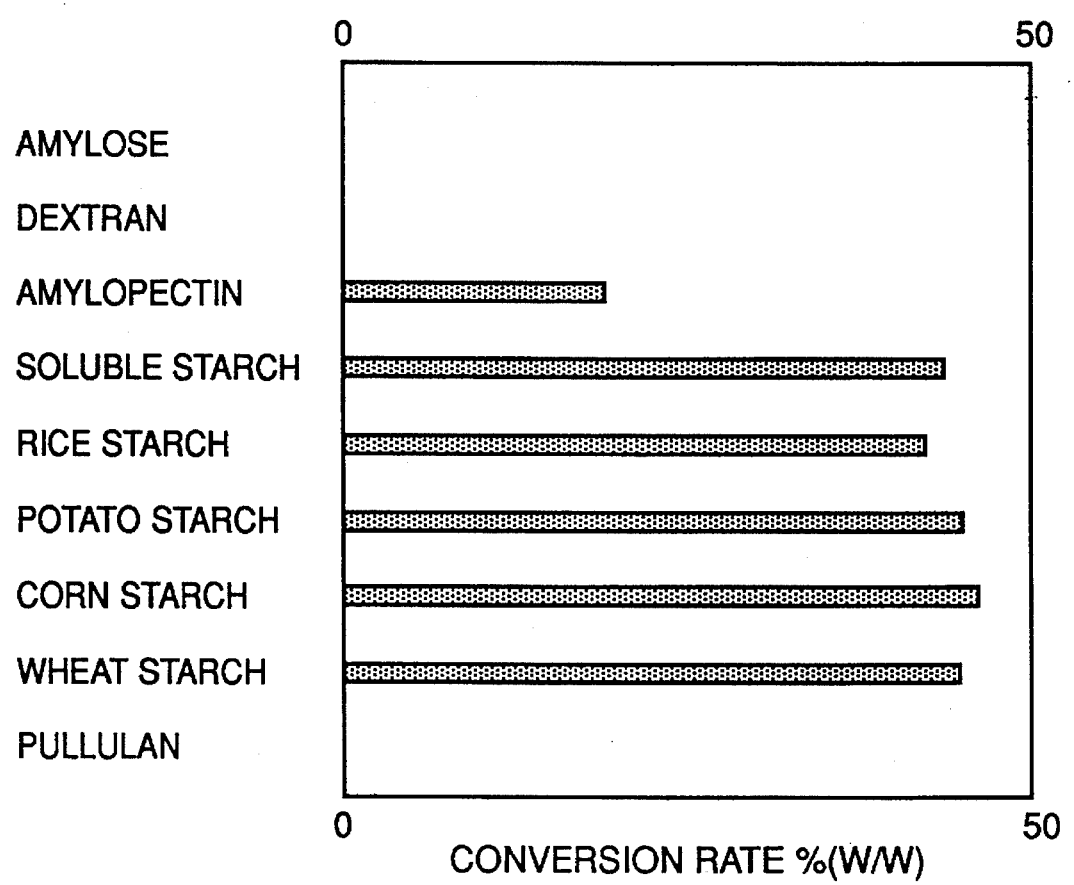
FIG. 4 shows the results of substrate specifically for α-cyclodextrin formation by the CGTase.

FIG. 4 shows the results of substrate specificity for α-cyclodextrin formation by the CGTase. 10 units of the CGTase was added to 1% of each substrate, prepared in 50 mM phosphate buffer (pH 6.0) and held at 37° C. for 20 hrs. Most of used starch reveals almost same specificity and this fact means any kind of used in this test can be freely used for the substrate for α-cyclodextrin formation by the CGTase. Conversion rate in FIG. 4 means percent of the weight of produced α-cyclodextrin from substrate to weight of added substrate.

EXAMPLE 6

This example illustrates the results of α-cyclodextrin formation. As starch is an inexpensive raw material, the production of α-cyclodextrin at a high concentration of starch has significant economical advantage on an industrial scale.

By raising the concentration of starch from 1% to 10%, a higher concentration of α-cyclodextrin was attained. Further increase, however, was not observed above 10%.

Figure 5:
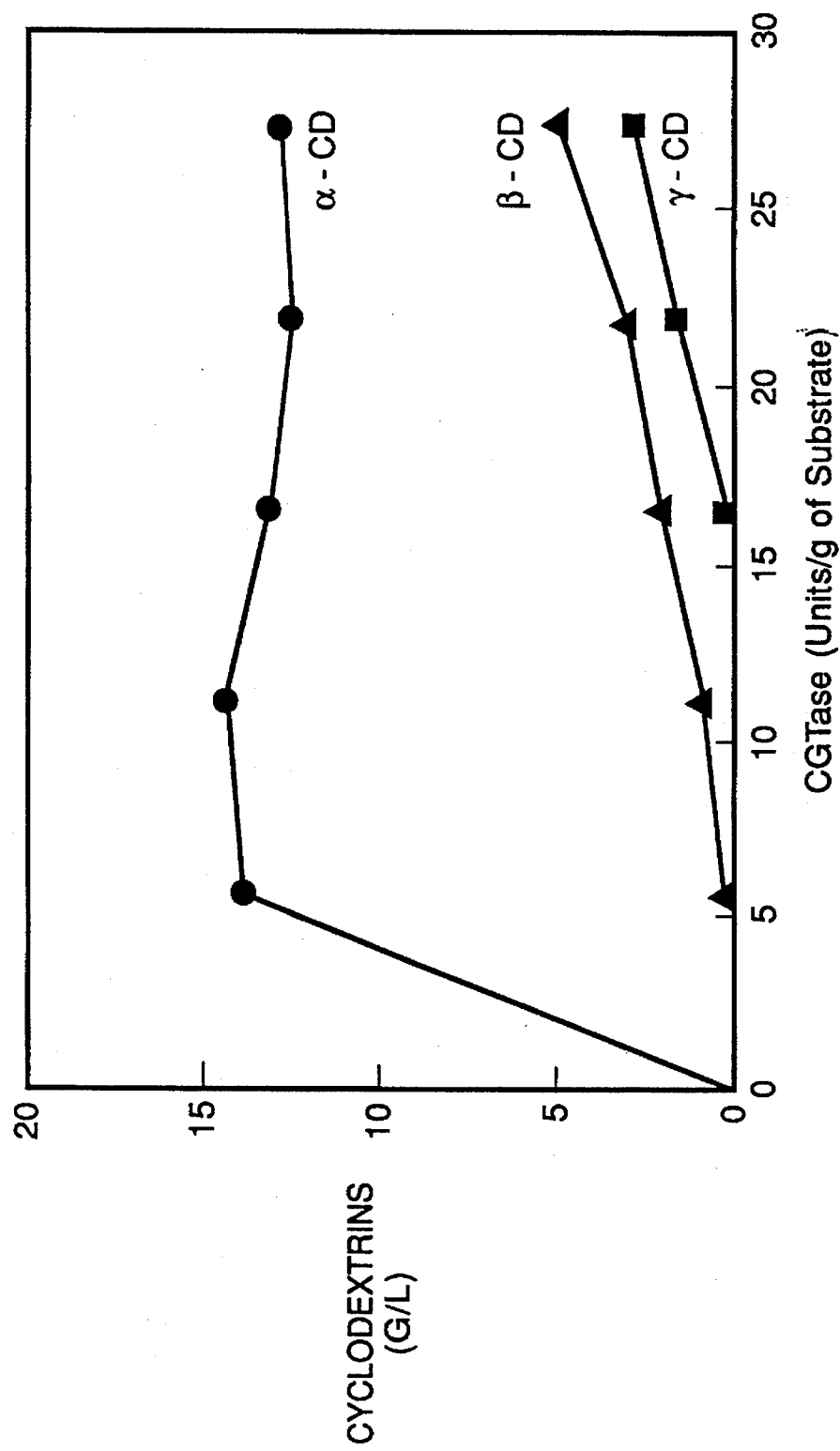
FIG. 5 shows the optimum ratio of enzyme to substrate was around 10 units/g of substrate in order to maximize synthesis of α-cyclodextrin and to minimize that of β- and γ-cyclodextrin at the same time.

When the ratio of enzyme to substrate was changed while maintaining the concentration of substrate at 10%, α-cyclodextrin was the only product at lower concentration levels of CGTase. As shown in FIG. 5, the optimum ratio of enzyme to substrate was around 10 units/g of substrate in order to maximize synthesis of α-cyclodextrin and to minimize that of β- and γ-cyclodextrin at the same time.

Figure 6:
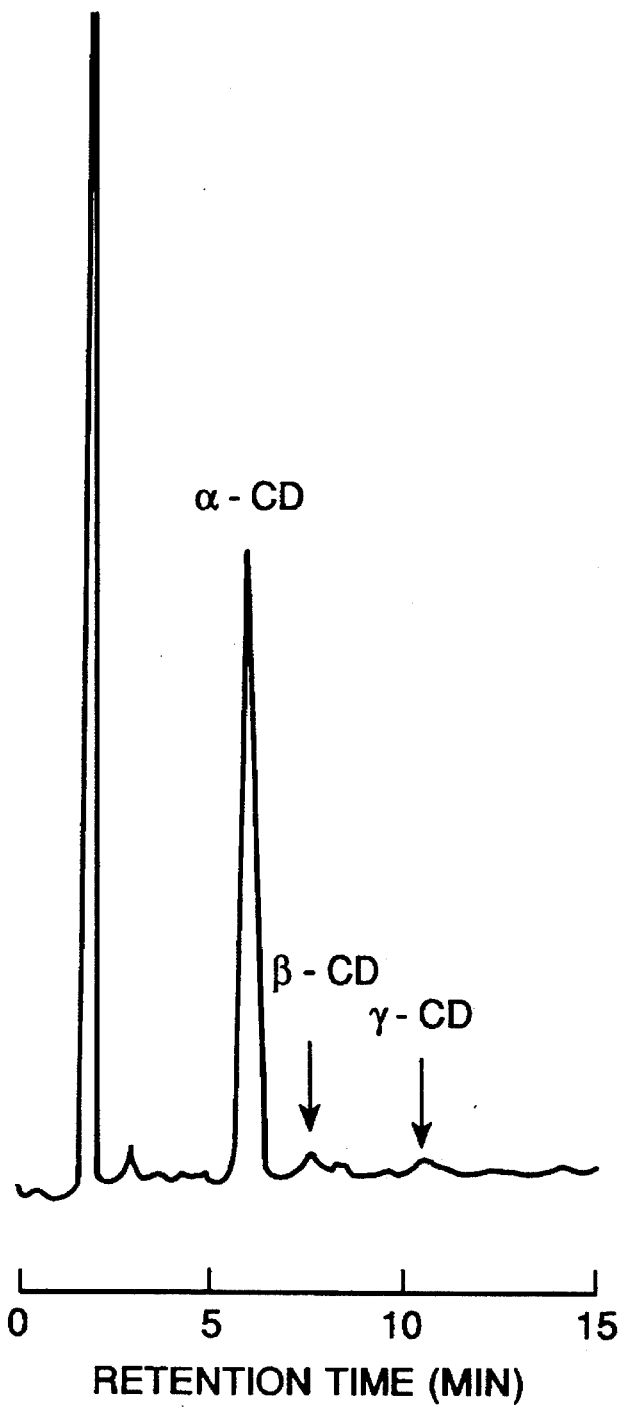
FIG. 6 shows the formation of cyclodextrins after 19 hr.

FIG. 6 shows the formation of cyclodextrins after 19 hr. Reaction conditions are as follows: 10% corn starch; 10 units of CGTase/g of corn starch; pH 6.0; 40° C. The ratio cyclodextrins at that time is α:β:γ=96.5:3.5:0.

The estimated concentration of α-cyclodextrin in FIG. 6 was about 15 gram. Thus, 15 gram of α-cyclodextrin was produced from 100 gram of corn starch under the above conditions.

Highly purified α-cyclodextrin can be easily prepared by concentration from α-cyclodextrin in the reaction mixture, produced under the above conditions after removal of remaining starch, since the proportion of α-cyclofextrin in reaction mixture occupies at least 95% of the total weight of the cyclodextrin mixture and nearly close to 100 percent.

Accordingly, it is possible to eliminate complicated processes, such as gel filtration and solvent precipitation, currently used in manufacturing α-cyclodextrin.

The most important property of the CGTase produced by *Klebsiella oxytoca* No. 19-1 is its ability to produce large amounts of almost exclusively α-cyclofextrin from starch in a short reaction time without the aid of solvents or chemical compounds, so that the downstream process involved in recovery α-cyclodextrin from the mixture of cyclodextrins will be very simplified. Thus, it may be unnecessary to purify further α-cyclodextrin from the mixture of cyclodextrins when the enzyme is used under the conditions exemplified herein. The mixture may be used in all but the most purity-strict applications.

We claim:

1. An isolated microorganism which produces a cyclodextrin glycosyltransferase when cultivated with starch, in the presence of a nitrogen source under aerobic conditions, said cyclodextrin glycosyltransferase converts starch to cyclodextrin which is at least 95% α-cyclodextrin; said microorganism belonging to the genus *Klebsiella* species *oxytoca*, wherein said microorganism is *Klebsiella oxytoca* No. 19-1 (KCCM 1002).

2. A biologically pure culture of *Klebsiella oxytoca* which produces a cyclodextrin glycosyltransferase when cultivated with starch, in the presence of a nitrogen source under aerobic conditions, said cyclodextrin glycosyltransferase converts starch to cyclodextrin, which is at least 95% α-cyclodextrin, wherein said *Klebsiella oxytoca* is *Klebsiella oxytoca* No. 19-1 (KCCM 1002).

3. An isolated gram negative microorganism which hydrolyzes pectate, grows at 10° C., is fecal coliform positive and produces cyclodextrin glycosyltransferase, when cultivated with starch, in the presence of a nitrogen source under aerobic conditions, said cyclodextrin glycosyltransferase converts starch to cyclodextrin which is at least 95% α-cyclodextrin, wherein said microorganism is *Klebsiella oxytoca* No. 19-1 (KCCM 1002).

4. A biologically pure culture of a gram negative microorganism which hydrolyzes pectate, grows at 10° C., is fecal coliform positive and produces cyclodextrin glycosyltransferase when cultivated with starch, in the presence of a nitrogen source under aerobic conditions, said cyclodextrin glycosyltransferase converts starch to cyclodextrin which is at least 95% α-cyclodextrin wherein said microorganism is *Klebsiella oxytoca* No. 19-1 (KCCM 1002).

5. A biologically pure culture of *Klebsiella oxytoca* No. 19-1 (KCCM 1002).

6. Isolated *Klebsiella oxytoca* No. 19-1 (KCCM 1002).

* * * * *